(12) United States Patent
Alsahhaf

(10) Patent No.: US 9,375,189 B1
(45) Date of Patent: Jun. 28, 2016

(54) X-RAY STICK MARKER

(71) Applicant: Abdulmuhsen A. Alsahhaf, Safat (KW)

(72) Inventor: Abdulmuhsen A. Alsahhaf, Safat (KW)

( * ) Notice: Subject to any disclaimer, the term of this patent is extended or adjusted under 35 U.S.C. 154(b) by 0 days.

(21) Appl. No.: 14/829,431

(22) Filed: Aug. 18, 2015

(51) Int. Cl.
| | |
|---|---|
| *B43K 5/00* | (2006.01) |
| *B43K 23/02* | (2006.01) |
| *A61B 17/28* | (2006.01) |
| *A61B 17/10* | (2006.01) |
| *A61B 10/02* | (2006.01) |
| *A61B 17/06* | (2006.01) |
| *A61B 6/10* | (2006.01) |
| *A61B 19/00* | (2006.01) |
| *A61B 17/00* | (2006.01) |

(52) U.S. Cl.
CPC . *A61B 6/10* (2013.01); *A61B 19/54* (2013.01); *A61B 2017/00473* (2013.01); *A61B 2019/545* (2013.01)

(58) Field of Classification Search
CPC ...... A61B 19/54; A61B 17/10; A61B 17/064; A61B 17/068; A61B 10/02
USPC .................. 401/6, 196–206; 606/64, 97, 142; 600/554
See application file for complete search history.

(56) References Cited

U.S. PATENT DOCUMENTS

| | | | | |
|---|---|---|---|---|
| 5,902,310 | A * | 5/1999 | Foerster | A61K 49/006 606/142 |
| 8,152,401 | B2 * | 4/2012 | Sokoloff | B43K 1/12 401/198 |
| 8,798,716 | B1 | 8/2014 | DeSena et al. | |
| 2005/0251111 | A1 * | 11/2005 | Saito | A61B 17/29 606/1 |
| 2007/0203504 | A1 * | 8/2007 | Denny | A61B 90/80 606/116 |
| 2008/0101846 | A1 * | 5/2008 | Brooks | B43K 23/001 401/131 |
| 2009/0253981 | A1 * | 10/2009 | Hamilton | A61M 35/006 600/414 |
| 2011/0282446 | A1 * | 11/2011 | Schulte | A61B 17/00491 623/11.11 |
| 2012/0130269 | A1 * | 5/2012 | Rea | A61B 5/0488 600/554 |
| 2013/0096459 | A1 * | 4/2013 | Vetter | A61B 10/06 600/567 |
| 2015/0086258 | A1 * | 3/2015 | Bezuhly | B43K 8/003 401/198 |
| 2015/0272571 | A1 * | 10/2015 | Leimbach | A61B 17/068 227/175.1 |
| 2015/0297217 | A1 * | 10/2015 | Huitema | A61B 17/068 227/177.1 |
| 2015/0297219 | A1 * | 10/2015 | Shelton, IV | A61B 17/068 227/176.1 |
| 2015/0297230 | A1 * | 10/2015 | Schellin | A61B 17/068 227/176.1 |
| 2015/0297231 | A1 * | 10/2015 | Huitema | A61B 17/068 228/176.1 |

FOREIGN PATENT DOCUMENTS

WO   WO 00/24332 A1   5/2000

\* cited by examiner

*Primary Examiner* — Mark A Laurenzi
*Assistant Examiner* — Thomas M Abebe
(74) *Attorney, Agent, or Firm* — Richard C. Litman

(57) ABSTRACT

The x-ray stick marker includes a shaft having a proximal end, a distal end, and a lumen extending through the shaft between the proximal end and the distal end. A handle is disposed at the proximal end of the shaft and a marking tip is disposed at the distal end of the shaft. The handle includes an actuating button configured to control the release of the marking tip. The marking tip is configured for marking the skin of the patient. To avoid exposure to radiation, a user may maintain a suitable distance from the patient when positioning the marking tip on a designated location of the patient's skin for drawing a mark thereon.

9 Claims, 5 Drawing Sheets

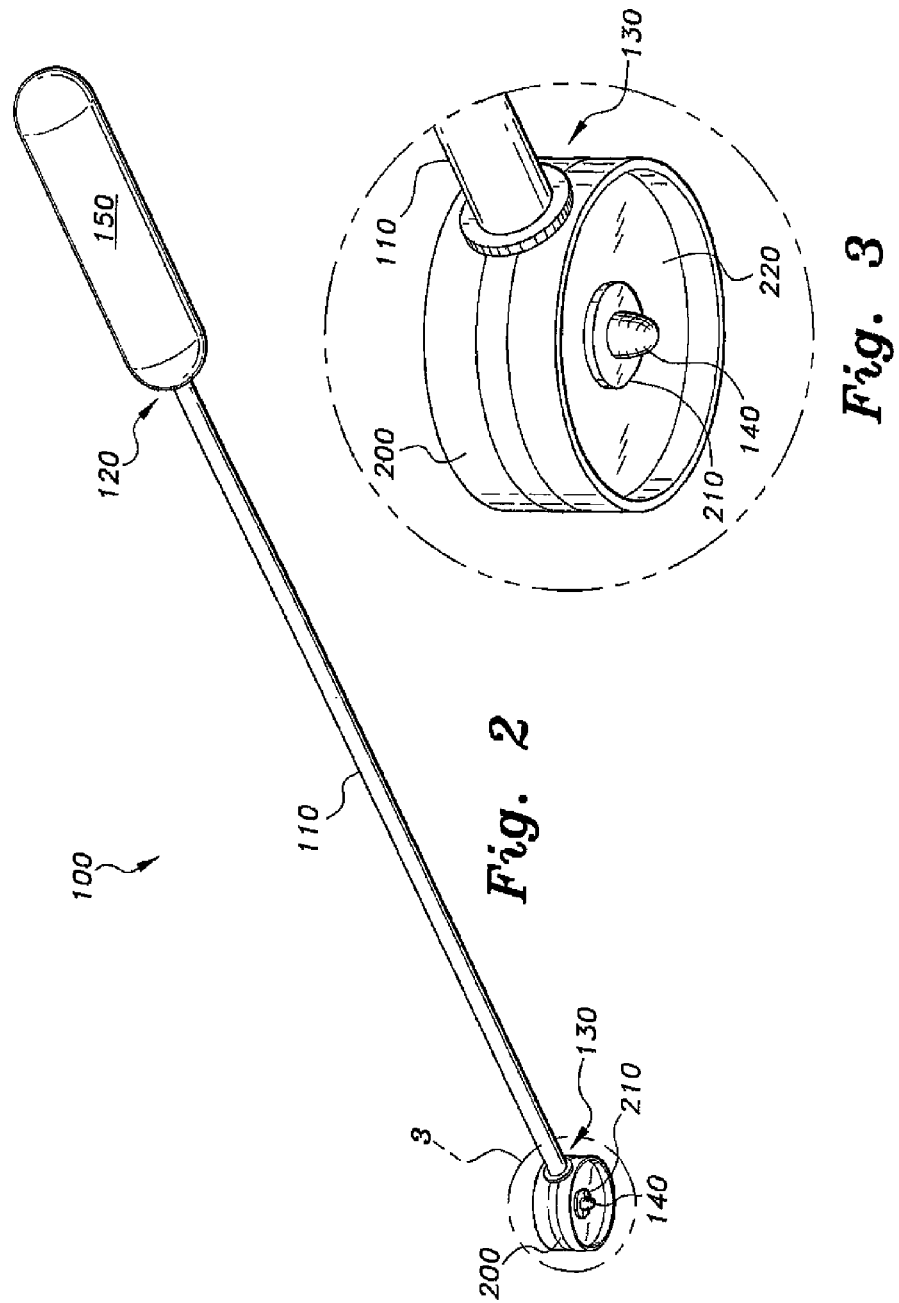

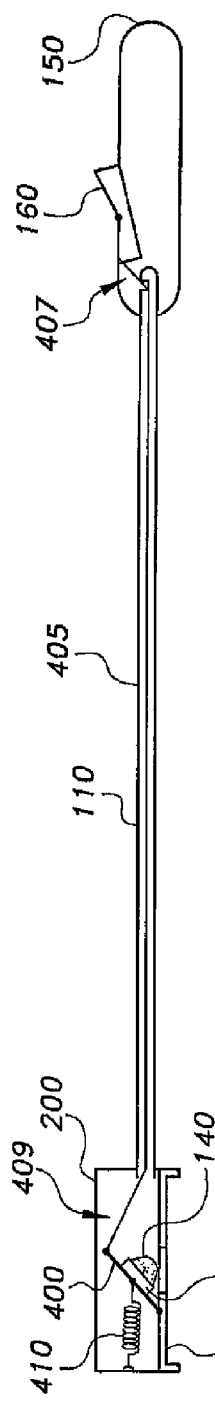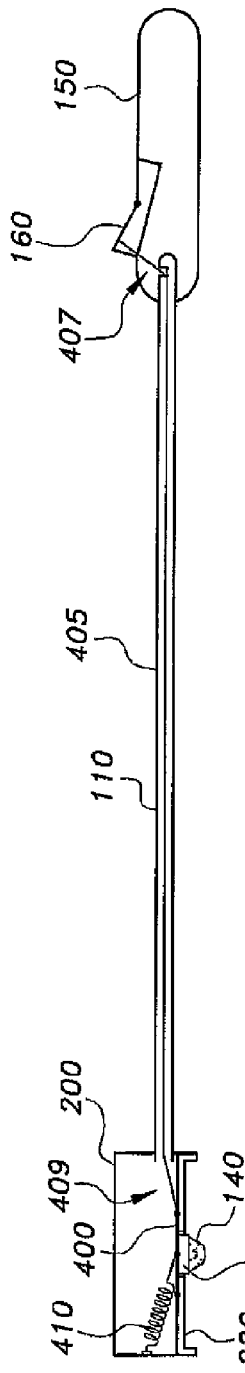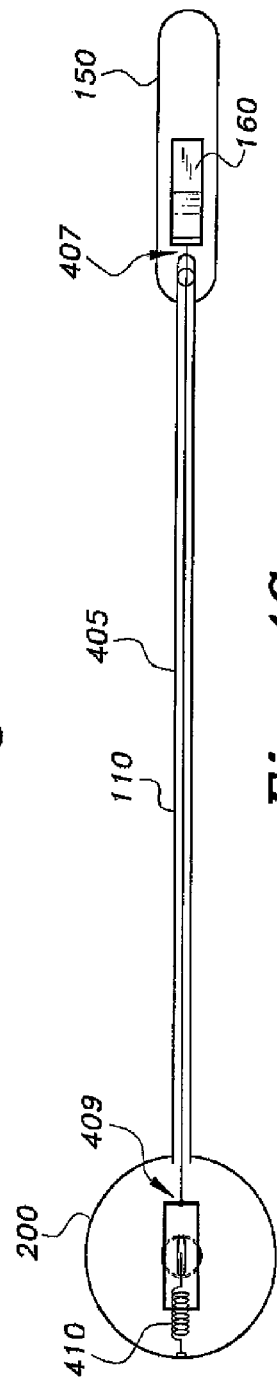

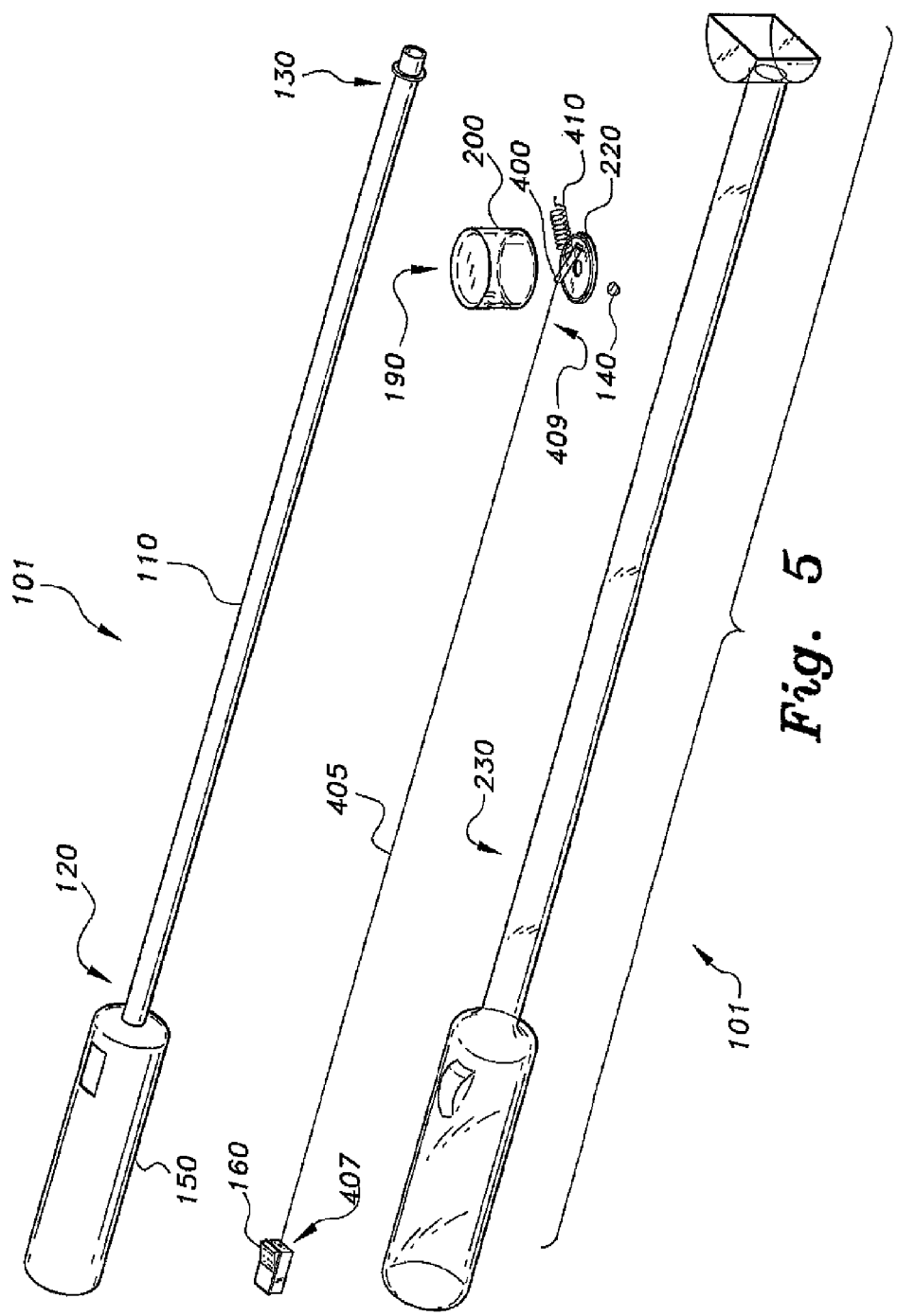

X-RAY STICK MARKER

BACKGROUND OF THE INVENTION

1. Field of the Invention

The present invention relates to medical devices and, particularly, to a skin-marking tool for use in marking the skin of a patient undergoing medical procedures.

2. Description of the Related Art

Many medical procedures ranging from injections and surgery to resetting a broken bone require the use of x-rays to determine the nature and the location of the injury. Despite the use of lead vests and protective eye wear to shield radiosensitive organs, such as the thyroid glands and eyes, many doctors and their staff are unnecessarily exposed to a large degree of radiation when using x-rays through indirect scattered radiation exposure, which typically results from radiation being reflected from a patient's body toward the doctor and/or his/her staff positioned around the patient.

Further, many medical practitioners are exposed to radiation multiple times during each procedure while standing next to the x-ray machine. For example, radiation exposure typically increases when a doctor is required to stand next to the patient when making his/her initial entry mark on the patient's body, such as for an incision or a needle entry point. This is typically done with the use of a metal device, such as artery forceps, which is usually very short, and as such, require the doctor and his/her staff to stand close to the patient and the x-ray machine until the doctor determines the location of the entry point and uses a sterile ink marker to mark that particular spot on the patient's body. The closeness of the medical personnel to the patient significantly increases the exposure of the medical personnel to radiation.

Thus, an x-ray stick marker solving the aforementioned problems is desired.

SUMMARY OF THE INVENTION

The x-ray stick marker can include a shaft having a proximal end and a distal end, a handle disposed at the proximal end of the shaft, and a marking tip disposed at the distal end, the marking tip configured for marking the skin of a patient. The distal end can be circular. The handle can be in communication with the marking tip. An actuating button on the handle is configured to control the release of the marking tip onto the patient's skin. The distal end can include a radiopaque portion that is visible on x-rays. The length of the x-ray stick marker can be about 80 cm in length or any appropriate length to allow a user to maintain a suitable distance from the patient and avoid any unnecessary exposure to radiation when positioning the at least one marking tip on a designated location of the patient's skin for drawing a mark thereon.

These and other features of the present invention will become readily apparent upon further review of the following specification and drawings.

BRIEF DESCRIPTION OF THE DRAWINGS

FIG. 2 is a bottom, perspective view of an x-ray stick marker having an exposed marking tip, according to the present invention.

FIG. 3 is an enlarged bottom view of an exposed marking tip positioned at the distal end of an x-ray marker, according to the present invention.

FIG. 4A is a side, schematic view of an x-ray stick marker having a retracted marking tip, according to the present invention.

FIG. 4B is a side, schematic view of an x-ray sticker maker having an exposed marking tip, according to the present invention.

FIG. 4C is a top view of an x-ray stick marker, according to the present invention.

FIG. 5 is a top view of a kit for assembling an x-ray stick marker, according to the present invention.

Similar reference characters denote corresponding features consistently throughout the attached drawings.

DETAILED DESCRIPTION OF THE PREFERRED EMBODIMENTS

Figure 1:
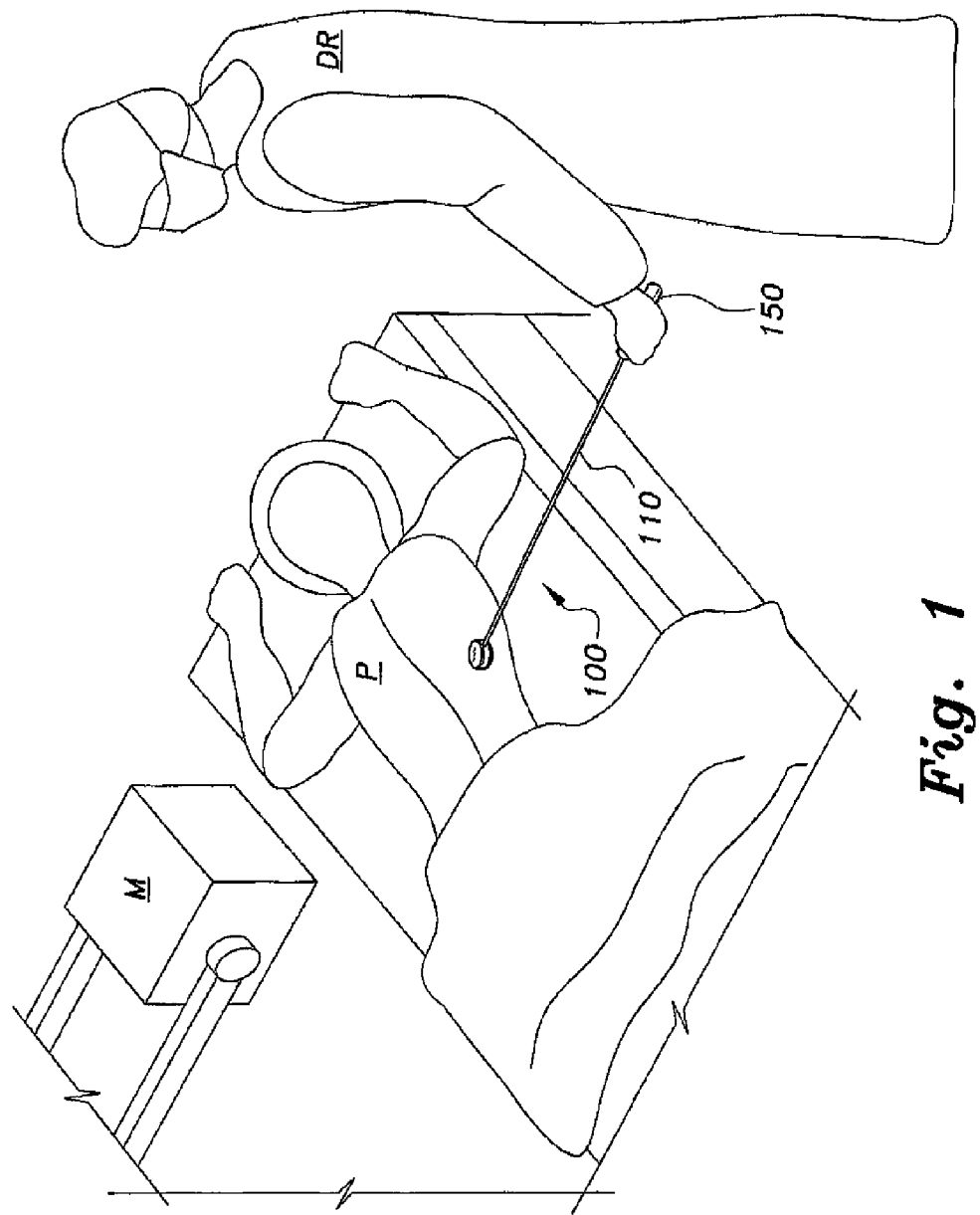
FIG. 1 is an environmental, top view of an x-ray stick marker, according to the present invention.
Figure 6:
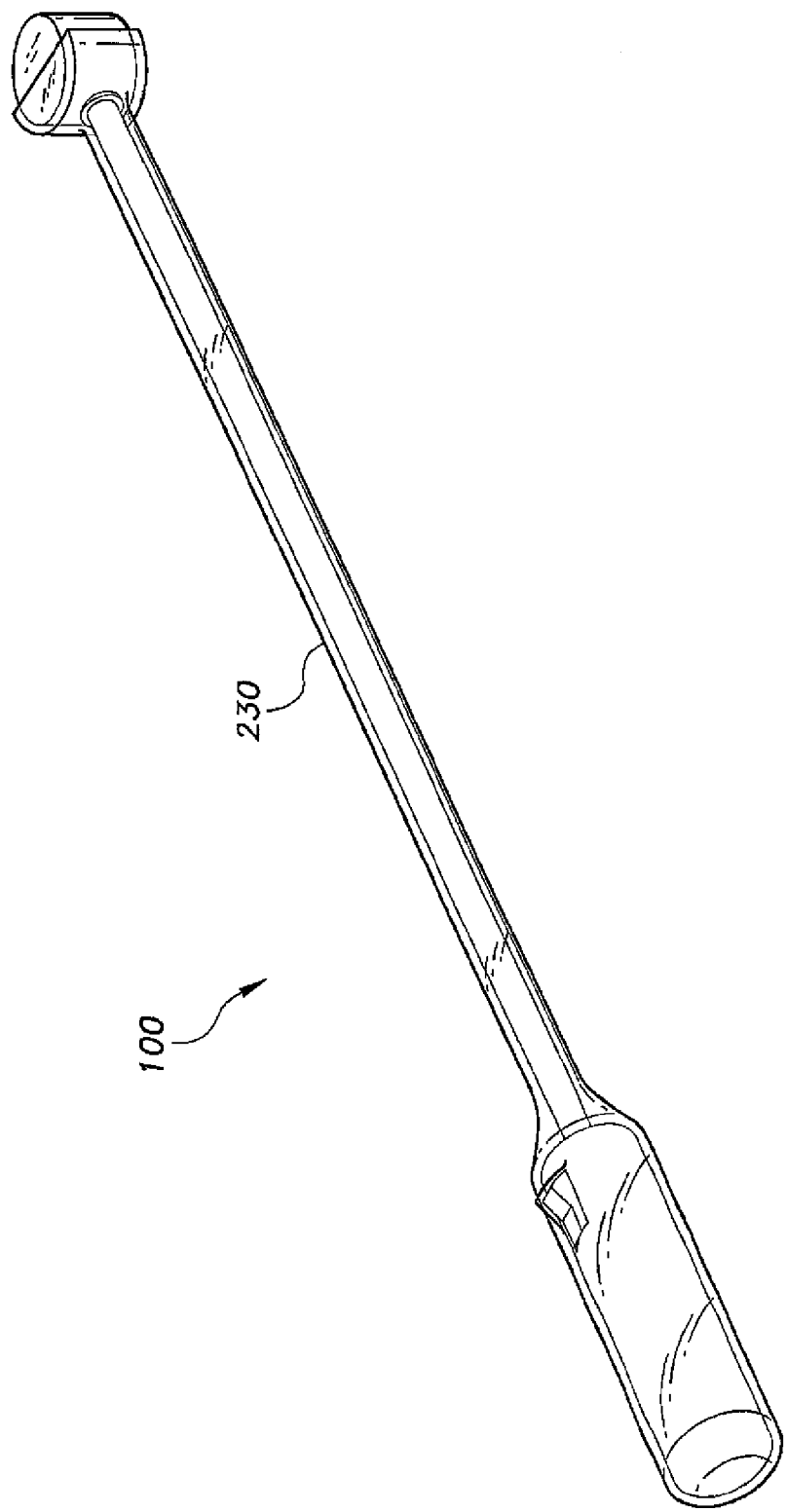
FIG. 6 is a top, perspective view of an x-ray stick marker having a sleeve, according to the present invention.

Referring to FIGS. 1 through 6, an x-ray stick marker 100 is generally illustrated. The x-ray stick marker 100 can include a shaft 110 having a proximal end 120, a distal end 130, a handle 150 disposed at the proximal end 120 of the shaft 110, a marking tip 140 at the distal end 130 of the shaft 110, and a lumen extending therethrough. The marking tip 140 is configured for marking the skin of a patient P. The distal end 130 can have a radiopaque portion that is visible on x-rays. To avoid exposure to radiation, a user may maintain a suitable distance from the patient P when positioning the marking tip 140 on a designated location of the patient's P skin for drawing a mark thereon. The x-ray stick marker 100 can be used by interventional physicians, such as anesthesiologists, radiologists, cardiologists, orthopedic surgeons, neurosurgeons, plastic surgeons, and/or vascular doctors.

As is illustrated in FIGS. 4A through 4C, the handle 150 can include an actuating button 160, such as a rocker switch, configured to control the release of the marking tip 140. Once released, the marking tip 140 can be used to mark the patient's skin. For example, the actuating button 160 can be in communication with the marking tip 140 by connecting piece 405 in the lumen of the shaft 110. Connecting piece 405 can be, for example, a string, cord, wire, thread, or thread-like material. Connecting piece 405 can have a first end 407 coupled to the actuating button 160 and a second end 409 coupled to a lever 400. The lever 400 is in communication with a resilient member 410, such as a spring or elastic material, which is connected to a ring member 200 and remains compressed until the actuating button 160 is manipulated. The actuating button 160 can be spring-loaded.

As illustrated in FIG. 4B, pressing on the actuator button 160 can exert tension on the connecting piece 405, which, in turn, can pull on the lever 400, such as in a downward direction away from the ring member 200 and, in turn, cause the resilient member 410 to expand so as to allow the marking tip 140 to move downward toward the target location on the patient's P skin. For example, after the correct location for the incision has been determined through the use of an x-ray machine M, the doctor DR can press the actuator button 160 to lower the marking tip 140 onto the patient's body so as to mark the location of the incision or the injection site. After marking the location for the incision, the doctor DR can release the actuator button 160, which, in turn, can release tension on the connecting piece 405 and cause the resilient member 410 to compress and lift the lever 400, such as in an upward direction, toward the ring member 200 and lift the marking tip 140 away from the skin of the patient.

The shaft 110 of the x-ray stick marker 100 can be formed from any suitable medical grade material, such as plastic.

Preferably, the shaft 110 is a disposable plastic. It is to be noted that the shaft 110 can be adjustable so as to reach a desired length. The length of the x-ray stick marker 100 or the shaft 110 alone can be about 80 cm in length, or any suitable length to allow a user to maintain a suitable distance from the patient P when positioning the marking tip 140 on a designated location of the patient's skin for drawing a mark thereon. A length of at least 80 cm in addition to the length of a doctor's DR arm can be about one meter, which can be sufficient to protect the doctor DR from scattered radiation exposure. As such, indirect, scattered radiation exposure can be reduced while the doctor DR marks the patient's skin with the x-ray stick marker 100.

The marking tip 140 can be a sterile marking tip disposed on the distal end 130. The marking tip 140 can include any type of suitable medical grade material that can leave a visible mark on a chosen bodily location. The marking tip 140 can include, for example, a sterile ink marker. The marking tip 140 can be coupled, such as removably coupled, to the lever 400 positioned at the distal end 130 of the shaft 110. Thus, after the marking tip 140 has been used to mark the patient P, the marking tip 140 can be removed and a new, sterile marking tip 140 can be inserted into the lever 400 for use on another patient.

The ring member 200 can include a cover member 190 extending over the marking tip 140, a bottom member 220, a circular portion 210, the lever 400, and the resilient member 410. The cover member 190 can be detachable. The ring member 200 can be made from any suitable medical grade material and can include a radiopaque material, e.g., metal, which can obstruct the passage of radiant energy, such as x-rays from an x-ray machine M. For example, at least a portion of the circular portion 210 can be radiopaque. The radiopaque portion can be X-shaped or cross-shaped and aligned with the marking tip 140 to better indicate the position of the marking tip 140. As such, the position of the marking tip 140 can be identified during use of a fluoroscopy or x-ray machine M to facilitate positioning of the marking tip 140 on a specific location of the patient's body. Further, a sleeve 230, such as a sterile plastic cover, can cover the entire x-ray stick marker 100 along with the actuating button 160 and the handle 150, so as to protect the x-ray stick marker 100 from contamination.

The handle 150 positioned at the proximal end 120 of the shaft 110 can be curved. The handle 150 can be formed from any suitable, medical grade material, such as plastic, capable of securely supporting the shaft 110 and the marking tip 140 disposed on the distal end 130 of the shaft 110. The handle 150 can have any suitable length, such as a length of six inches.

The x-ray stick marker 100 can be provided in a kit 101, as illustrated in FIG. 5. The kit 101 can include the x-ray stick marker 100 and one or more marking tips 140. (desirably five to ten marking tips 140), which can be removably attached to the x-ray stick marker 100. The shaft 110 can be used with a different marking tip 140 for each use. The kit can also include the sleeve 230.

By way of operation, once the marking tip 140 has been removably coupled to the lever 400 at the distal end 130 of the shaft 110, the doctor DR or his/her staff can activate the x-ray machine M so as to determine the location of the injury. Upon finding the correct location for the incision, the doctor DR can press the actuator button 160 to pull the connecting piece 405 and the lever 400. This movement can cause the resilient member 410 to expand away from the ring member 200 and allow the marking tip 140 to move downward toward the patient's P body. The doctor DR can then use the x-ray stick marker 100 to mark the location of the incision or the region for the medical operation while keeping a suitable distance from the x-ray machine.

After the incision location has been marked, the doctor DR can release the actuator button 160 so as to release the tension on the connecting piece 405. This can cause the resilient member 410 to compress which, in turn, can pull the lever 400 to move the marking tip 140 away from the patient P. The length of the x-ray stick marker 100 can allow the doctor DR to maintain a suitable distance from the patient P and avoid exposure to radiation when positioning the marking tip 140 on a designated location of the patient's skin for drawing a mark thereon. As such, indirect, scattered radiation exposure can be reduced while the doctor DR marks the patient's skin with the x-ray stick marker 100.

It is to be understood that the present invention is not limited to the embodiments described above, but encompasses any and all embodiments within the scope of the following claims.

I claim:

1. An x-ray stick marker for marking the skin of a patient, consisting of:
    a shaft having a proximal end and a distal end;
    a marking tip disposed at the distal end of the shaft, the marking tip attached to an adjustable lever, the marking tip includes medical grade material that can leave a visible mark on a selected body location, wherein the marking tip is a sterile ink marker;
    a handle disposed at the proximal end of the shaft, the handle including an actuating button in communication with the adjustable lever;
    a ring member including a radiopaque material;
    a connecting piece, the connecting piece having a first end coupled to the actuating button and a second end coupled to the adjustable lever; and
    a resilient member, the resilient member having a first end coupled to the ring member and a second end coupled to the adjustable lever,
    wherein movement of the actuating button exerts force on the connecting piece, which, in turn, moves the adjustable lever away from the ring member, which, in turn, permits the resilient member to expand, thereby allowing the marking tip to move away from the ring and onto the patient's body.

2. The x-ray stick marker according to claim 1, wherein the marking tip is removably attached to the adjustable lever.

3. The x-ray stick marker according to claim 1, wherein the shaft has a length of at least about 80 cm.

4. The x-ray stick marker according to claim 1, wherein the shaft has an adjustable length.

5. The x-ray stick marker according to claim 1, wherein the shaft includes a plastic material.

6. The x-ray stick marker according to claim 1, wherein the connecting piece is disposed within a lumen of the shaft.

7. The x-ray stick marker according to claim 1, wherein the resilient member is a spring.

8. The x-ray stick marker according to claim 1, wherein the ring member includes a detachable cover member.

9. A kit for assembling an x-ray stick marker, comprising:
    an x-ray stick marker consisting of:
        i) a shaft having a proximal end, a distal end,
        ii) a handle disposed at the proximal end of the shaft, the handle including an actuating button, a lever positioned in communicating relation to the actuating button,
        iii) a ring member including a radiopaque material disposed at the distal portion of the shaft, iv) a resilient member connecting the lever to the ring member,
v) a connecting piece positioned inside the lumen of the shaft, the connecting piece having a first end coupled to the actuating button and a second end coupled to the lever;

wherein movement of the actuating button exerts force on the connecting piece, which, in turn, moves the adjustable lever away from the ring member, which, in turn, permits the resilient member to expand, thereby allowing the marking tip to move away from the ring and onto the patient's body;

a plurality of marking tips configured for removable attachment to the lever, wherein each of the plurality of the marking tips includes a sterile ink marker; and a sleeve configured for surrounding the x-ray stick marker and protecting the x-ray stick marker from contamination.

* * * * *